US010341790B2

(12) United States Patent
Shennib

(10) Patent No.: US 10,341,790 B2
(45) Date of Patent: Jul. 2, 2019

(54) SELF-FITTING OF A HEARING DEVICE

(71) Applicant: iHear Medical, Inc., San Leandro, CA (US)

(72) Inventor: Adnan Shennib, Oakland, CA (US)

(73) Assignee: iHear Medical, Inc., San Leandro, CA (US)

( * ) Notice: Subject to any disclaimer, the term of this patent is extended or adjusted under 35 U.S.C. 154(b) by 0 days.

(21) Appl. No.: 15/368,342

(22) Filed: Dec. 2, 2016

(65) Prior Publication Data

US 2017/0164124 A1 Jun. 8, 2017

Related U.S. Application Data

(60) Provisional application No. 62/263,560, filed on Dec. 4, 2015.

(51) Int. Cl.
*H04R 25/00* (2006.01)

(52) U.S. Cl.
CPC .......... *H04R 25/70* (2013.01); *H04R 25/554* (2013.01); *H04R 2225/43* (2013.01)

(58) Field of Classification Search
CPC .... H04R 25/70; H04R 25/554; H04R 25/558; H04R 25/305; H04R 25/505; H04R 25/30;
(Continued)

(56) References Cited

U.S. PATENT DOCUMENTS 4,759,070 A 7/1988 Voroba
5,197,332 A 3/1993 Shennib
(Continued)

FOREIGN PATENT DOCUMENTS

EP 2515303 A1 * 10/2012 ............ G11B 20/10
JP H10126895 A 5/1998
(Continued)

OTHER PUBLICATIONS

Internet Archive, World Health Organization website "Grades of Hearing Impairment". Retrieved from <https://web.archive.org/web/20121024120107/http://www.who.int/pbd/deafness/hearing_impairment_grades/en> on Aug. 27, 2015.
(Continued)

*Primary Examiner* — Curtis A Kuntz
*Assistant Examiner* — Julie X Dang
(74) *Attorney, Agent, or Firm* — Dorsey & Whitney LLP

(57) ABSTRACT

Disclosed herein are systems and methods enabling self-fitting by a non-expert consumer. The method in some examples involves transmitting a wireless command by a computing device to a hearing device in-situ to produce a sequence of test audio signals corresponding to natural sound segments, while allowing the consumer to adjust fitting parameters based on perceptual assessment of hearing device output. The sound segments may represent a practical range of sounds within the normal human auditory range, with each sound segment selected to correspond to one or more fitting parameters of the programmable hearing device. The consumer is instructed to listen to the output of the in-situ hearing device and adjust controls on the personal computer's graphical user interface related to corresponding fitting parameters. The systems and methods disclosed herein allow dispensing or adjusting of hearing devices without requiring specialized instruments or clinical settings.

21 Claims, 12 Drawing Sheets

(58) Field of Classification Search
CPC . H04R 2225/43; H04R 2225/55; H04R 25/50
USPC .................................................. 381/412–414
See application file for complete search history.

(56) References Cited

U.S. PATENT DOCUMENTS

| | | | |
|---|---|---|---|
| 5,327,500 | A | 7/1994 | Campbell |
| 5,553,152 | A | 9/1996 | Newton |
| 5,645,074 | A | 7/1997 | Shennib et al. |
| 5,659,621 | A | 8/1997 | Newton |
| 5,701,348 | A | 12/1997 | Shennib et al. |
| 5,785,661 | A | 7/1998 | Shennib et al. |
| 5,928,160 | A | 7/1999 | Clark |
| 6,118,877 | A * | 9/2000 | Lindemann ............ H04R 25/70 381/23.1 |
| 6,137,889 | A | 10/2000 | Shennib et al. |
| 6,212,283 | B1 | 4/2001 | Fletcher et al. |
| 6,319,207 | B1 | 11/2001 | Naidoo |
| 6,359,993 | B2 | 3/2002 | Brimhall |
| 6,367,578 | B1 | 4/2002 | Shoemaker |
| 6,379,314 | B1 | 4/2002 | Horn |
| 6,382,346 | B2 | 5/2002 | Brimhall et al. |
| 6,428,485 | B1 | 8/2002 | Rho |
| 6,447,461 | B1 | 9/2002 | Eldon |
| 6,473,513 | B1 | 10/2002 | Shennib et al. |
| 6,522,988 | B1 | 2/2003 | Hou |
| 6,546,108 | B1 | 4/2003 | Shennib et al. |
| 6,574,342 | B1 * | 6/2003 | Davis .................... H04R 25/70 381/314 |
| 6,674,862 | B1 | 1/2004 | Magilen |
| 6,724,902 | B1 | 4/2004 | Shennib et al. |
| 6,840,908 | B2 | 1/2005 | Edwards et al. |
| 6,937,735 | B2 | 8/2005 | DeRoo et al. |
| 6,940,988 | B1 | 9/2005 | Shennib et al. |
| 6,978,155 | B2 | 12/2005 | Berg |
| 7,010,137 | B1 | 3/2006 | Leedom et al. |
| 7,016,511 | B1 | 3/2006 | Shennib |
| 7,037,274 | B2 | 5/2006 | Thoraton et al. |
| 7,113,611 | B2 | 9/2006 | Leedom et al. |
| 7,215,789 | B2 | 5/2007 | Shennib et al. |
| 7,260,232 | B2 | 8/2007 | Shennib |
| 7,298,857 | B2 | 11/2007 | Shennib et al. |
| 7,310,426 | B2 | 12/2007 | Shennib et al. |
| 7,321,663 | B2 | 1/2008 | Olsen |
| 7,362,875 | B2 | 4/2008 | Saxton et al. |
| 7,403,629 | B1 | 7/2008 | Aceti et al. |
| 7,424,123 | B2 | 9/2008 | Shennib et al. |
| 7,424,124 | B2 | 9/2008 | Shennib et al. |
| 7,580,537 | B2 | 8/2009 | Urso et al. |
| 7,664,282 | B2 | 2/2010 | Urso et al. |
| 7,854,704 | B2 | 12/2010 | Givens et al. |
| 7,913,696 | B2 | 3/2011 | Purcell et al. |
| 7,945,065 | B2 | 5/2011 | Menzl et al. |
| 8,073,170 | B2 | 12/2011 | Kondo et al. |
| 8,077,890 | B2 | 12/2011 | Schumaier |
| 8,155,361 | B2 | 4/2012 | Schindler |
| 8,184,842 | B2 | 5/2012 | Howard et al. |
| 8,243,972 | B2 | 8/2012 | Latzel |
| 8,284,968 | B2 | 10/2012 | Schumaier |
| 8,287,462 | B2 | 10/2012 | Givens et al. |
| 8,340,335 | B1 | 12/2012 | Shennib |
| 8,379,871 | B2 | 2/2013 | Michael et al. |
| 8,396,237 | B2 | 3/2013 | Schumaier |
| 8,447,042 | B2 | 5/2013 | Gurin |
| 8,467,556 | B2 | 6/2013 | Shennib et al. |
| 8,503,703 | B2 | 8/2013 | Eaton et al. |
| 8,571,247 | B1 | 10/2013 | Oezer |
| 8,718,306 | B2 | 5/2014 | Gommel et al. |
| 8,798,301 | B2 | 8/2014 | Shennib |
| 8,855,345 | B2 | 10/2014 | Shennib et al. |
| 9,031,247 | B2 | 5/2015 | Shennib |
| 9,060,233 | B2 | 6/2015 | Shennib et al. |
| 9,078,075 | B2 | 7/2015 | Shennib et al. |
| 9,107,016 | B2 | 8/2015 | Shennib |
| 9,253,583 | B2 | 2/2016 | Blamey et al. |
| 9,326,706 | B2 | 5/2016 | Shennib |
| 9,439,008 | B2 | 9/2016 | Shennib |
| 9,532,152 | B2 | 12/2016 | Shennib et al. |
| 2001/0008560 | A1 | 7/2001 | Stonikas et al. |
| 2001/0009019 | A1 | 7/2001 | Armitage |
| 2001/0040973 | A1 | 11/2001 | Fritz et al. |
| 2001/0051775 | A1 | 12/2001 | Rho |
| 2002/0027996 | A1 | 3/2002 | Leedom et al. |
| 2002/0085728 | A1 | 7/2002 | Shennib et al. |
| 2003/0007647 | A1 | 1/2003 | Nielsen et al. |
| 2003/0078515 | A1 | 4/2003 | Menzel et al. |
| 2004/0028250 | A1 | 2/2004 | Shim |
| 2004/0073136 | A1 | 4/2004 | Thornton et al. |
| 2004/0122873 | A1 | 6/2004 | Wright, Jr. et al. |
| 2004/0165742 | A1 | 8/2004 | Shennib et al. |
| 2005/0094822 | A1 * | 5/2005 | Swartz .................. A61B 5/121 381/56 |
| 2005/0226447 | A1 | 10/2005 | Miller, III |
| 2005/0245991 | A1 | 11/2005 | Faltys et al. |
| 2005/0249370 | A1 | 11/2005 | Shennib et al. |
| 2005/0259840 | A1 | 11/2005 | Gable et al. |
| 2005/0283263 | A1 | 12/2005 | Eaton et al. |
| 2006/0094981 | A1 | 5/2006 | Camp |
| 2006/0210090 | A1 * | 9/2006 | Shennib ................ A61B 5/121 381/67 |
| 2006/0210104 | A1 | 9/2006 | Shennib et al. |
| 2006/0291683 | A1 | 12/2006 | Urso et al. |
| 2007/0009126 | A1 | 1/2007 | Fischer et al. |
| 2007/0071265 | A1 | 3/2007 | Leedom et al. |
| 2007/0076909 | A1 | 4/2007 | Roeck et al. |
| 2007/0189545 | A1 | 8/2007 | Geiger et al. |
| 2007/0237346 | A1 | 10/2007 | Fichtl et al. |
| 2008/0137891 | A1 | 6/2008 | Vohringer |
| 2008/0240452 | A1 | 10/2008 | Burrows et al. |
| 2008/0273726 | A1 | 11/2008 | Yoo et al. |
| 2008/0298600 | A1 | 12/2008 | Poe et al. |
| 2009/0220099 | A1 | 9/2009 | Voix et al. |
| 2010/0040250 | A1 | 2/2010 | Gerbert |
| 2010/0119094 | A1 | 5/2010 | Sjursen et al. |
| 2010/0145411 | A1 | 6/2010 | Spitzer |
| 2010/0191143 | A1 | 7/2010 | Ganter |
| 2010/0226520 | A1 | 9/2010 | Feeley et al. |
| 2010/0239112 | A1 | 9/2010 | Howard et al. |
| 2010/0268115 | A1 | 10/2010 | Wasden et al. |
| 2010/0284556 | A1 * | 11/2010 | Young ................ H04R 25/558 381/314 |
| 2010/0290654 | A1 | 11/2010 | Wiggins et al. |
| 2011/0058697 | A1 | 3/2011 | Shennib et al. |
| 2011/0176686 | A1 | 7/2011 | Zaccaria |
| 2011/0188689 | A1 | 8/2011 | Beck et al. |
| 2011/0190658 | A1 | 8/2011 | Sohn et al. |
| 2011/0200216 | A1 | 8/2011 | Lee et al. |
| 2011/0206225 | A1 | 8/2011 | Møller et al. |
| 2011/0319018 | A1 * | 12/2011 | Kroman ............... H04R 25/554 455/41.1 |
| 2012/0051569 | A1 | 3/2012 | Blamey et al. |
| 2012/0095528 | A1 | 4/2012 | Miller, III et al. |
| 2012/0130271 | A1 | 5/2012 | Margolis et al. |
| 2012/0177212 | A1 * | 7/2012 | Hou ...................... H04R 25/70 381/60 |
| 2012/0177235 | A1 | 7/2012 | Solum |
| 2012/0183164 | A1 | 7/2012 | Foo et al. |
| 2012/0183165 | A1 | 7/2012 | Foo et al. |
| 2012/0189140 | A1 | 7/2012 | Hughes |
| 2012/0213393 | A1 | 8/2012 | Foo et al. |
| 2012/0215532 | A1 | 8/2012 | Foo et al. |
| 2012/0285470 | A9 | 11/2012 | Sather et al. |
| 2012/0302859 | A1 | 11/2012 | Keefe |
| 2013/0010406 | A1 | 1/2013 | Stanley |
| 2013/0177188 | A1 | 7/2013 | Apfel et al. |
| 2013/0182877 | A1 | 7/2013 | Angst et al. |
| 2013/0223666 | A1 | 8/2013 | Michel et al. |
| 2013/0243209 | A1 | 9/2013 | Zurbruegg et al. |
| 2013/0243227 | A1 | 9/2013 | Kinsbergen et al. |
| 2013/0243229 | A1 | 9/2013 | Shennib et al. |
| 2013/0294631 | A1 | 11/2013 | Shennib et al. |
| 2014/0003639 | A1 | 1/2014 | Shennib et al. |
| 2014/0150234 | A1 | 6/2014 | Shennib et al. |
| 2014/0153761 | A1 | 6/2014 | Shennib et al. |

(56) References Cited

U.S. PATENT DOCUMENTS

| | | |
|---|---|---|
| 2014/0153762 A1 | 6/2014 | Shennib et al. |
| 2014/0193008 A1 | 7/2014 | Zukic |
| 2014/0254843 A1 | 9/2014 | Shennib |
| 2014/0254844 A1 | 9/2014 | Shennib |
| 2015/0023512 A1 | 1/2015 | Shennib |
| 2015/0023534 A1 | 1/2015 | Shennib |
| 2015/0023535 A1 | 1/2015 | Shennib |
| 2015/0025413 A1 | 1/2015 | Shennib |
| 2015/0215714 A1 | 7/2015 | Shennib et al. |
| 2015/0256942 A1 | 9/2015 | Kinsbergen et al. |
| 2016/0066822 A1 | 3/2016 | Shennib et al. |
| 2016/0080872 A1 | 3/2016 | Shennib et al. |
| 2016/0166181 A1 | 6/2016 | Shennib |
| 2016/0198271 A1 | 7/2016 | Shennib |
| 2016/0337770 A1 | 11/2016 | Shennib |
| 2016/0350821 A1 | 12/2016 | Shennib et al. |
| 2017/0070833 A1 | 3/2017 | Shennib |

FOREIGN PATENT DOCUMENTS

| | | |
|---|---|---|
| JP | 2002259714 A | 9/2002 |
| JP | 2005286876 A | 10/2005 |
| JP | 2007028609 A | 2/2007 |
| JP | 2008109594 A | 5/2008 |
| KR | 1020050114861 A | 12/2005 |
| KR | 100955033 B1 | 4/2010 |
| KR | 1020100042370 A | 4/2010 |
| WO | 99/07182 A2 | 2/1999 |
| WO | 2010/091480 A1 | 8/2010 |
| WO | 2011128462 A2 | 10/2011 |
| WO | 2015009559 A1 | 1/2015 |
| WO | 2015009561 A1 | 1/2015 |
| WO | 2015009564 A1 | 1/2015 |
| WO | 2015009569 A1 | 1/2015 |
| WO | 2016044178 A1 | 3/2016 |

OTHER PUBLICATIONS

"Basic Guide to in Ear Canalphones", Internet Archive, Head-Fi.org, Jul. 1, 2012. Retrieved from http://web.archive.org/web/20120701013243/http:www.head-fi.org/a/basic-guide-to-in-ear-canalphones> on Apr. 14, 2015.

"dB HL—Sensitivity to Sound—Clinical Audiograms", Internet Archive, AuditoryNeuroscience.com, Apr. 20, 2013. Retrieved from <https://web.archive.org/web/20130420060438/http://www.auditoryneuroschience.com/acoustics/clinical_audiograms>on Apr. 14, 2015.

"International Search Report and Written Opinon", International Search Report and Written Opinion received for PCT Appl. PCT/US2016/064791 dated Feb. 16, 2017.

"Lyric User Guide", http://www.phonak.com/content/dam/phonak/b2b/C_M_tools/Hearing_Instruments/Lyric/documents/02-gb/Userguide_Lyric_V8_GB_FINAL_WEB.pdf, Jul. 2010.

"Methods for Calculation of the Speech Intelligibility Index", American National Standards Institute, Jun. 6, 1997.

"Specification for Audiometers", American National Standards Institute, Nov. 2, 2010.

"The Audiogram", Internet Archive, ASHA.org, Jun. 21, 2012, Retrieved from <https:/web.archive.org/web/20120621202942/http://www.asha.org/public/hearing/Audiogram> on Apr. 14, 2015.

"User Manual—2011", AMP Personal Audio Amplifiers.

Abrams, "A Patient-adjusted Fine-tuning Approach for Optimizing the Hearing Aid Response", The Hearing Review, Mar. 24, 2011, 1-8.

Amlani, et al., "Methods and Applications of the Audibility Index in Hearing Aid Selection and Fitting", Trends in Amplication 6.3 (2002) 81. Retrieved from <https://www.ncbi.nlm.nih.gov/pmc/articles/PMC4168961/> on Apr. 14, 2015.

Asha, "Type, Degree, and Configuration of Hearing Loss", American Speech-Language-Hearing Association; Audiology Information Series, May 2011, 1-2.

Convery, et al., "A Self-Fitting Hearing Aid: Need and Concept", http://tia.sagepubl.com, Dec. 4, 2011, 1-10.

Franks, "Hearing Measurements", National Institute for Occupational Safety and Health, Jun. 2006, 183-232.

Kiessling, "Hearing aid fitting procedures—state-of-the-art and current issues", Scandinavian Audiology vol. 30, Suppl 52, 2001, 57-59.

Kryter, , "Methods for the calculation and use of the articulation index", The Journal of the Acoustical Society of America 34.11 (1962): 1689-1697. Retrieved from <http://dx.doi.org/10.1121/1.1909094> on Aug. 27, 2015.

Nhanes, "Audiometry Procedures Manual", National Health and Nutrition Examination Survey, Jan. 2003, 1-105.

Sindhusake, et al., "Validation of self-reported hearing loss. The Blue Mountains hearing study", International Journal of Epidemiology 30.6 (2001 ): 1371-1378. Retrieved from <http://ije.oxfordjournals.org/content/30/6/1371.full> on Aug. 27, 2015.

Traynor, "Prescriptive Procedures", www.rehab.research.va.gov/mono/ear/traynor.htm, Jan. 1999, 1-16.

World Health Organization, "Deafness and Hearing Loss", www.who.int/mediacentre/factsheets/fs300/en/index.html, Feb. 2013, 1-5.

Ishikawa, et al.; "Cosmetology seeing from the standpoint of aesthetic science—aesthetics and amenity", Fragrance Journal vol. 20 No. 7, Japan, Jul. 1992, p. 62-p. 70.

Maeda, et al., "The Seasonal Features of Soundscape—Statistical Analysis of the Acoustical Environment of Daily Life Shown in the World of Haiku Using Hayashi's Quantification Theory", Kyushu Institute of Design—The Acoustical Society of Japan research presentation meeting lecture collected papers Autumn I, Japan, corporation Acoustical Society of Japan, Oct. 1992, p. 591-592.

* cited by examiner

SELF-FITTING OF A HEARING DEVICE

CROSS-REFERENCE TO RELATED APPLICATION(S)

This application claims the benefit under 35 U.S.C. 119 of the earlier filing date of U.S. Provisional Application No. 62/263,560 entitled "SELF-FITTING OF A HEARING DEVICE," filed Dec. 4, 2015. The aforementioned provisional application is hereby incorporated by reference in its entirety, for any purpose.

This application is related to U.S. Pat. No. 9,031,247, titled, "HEARING AID FITTING SYSTEMS AND METHODS USING SOUND SEGMENTS REPRESENTING RELEVANT SOUNDSCAPE," U.S. Pat. No. 9,107,016, titled, "INTERACTIVE HEARING AID FITTING SYSTEM AND METHODS," and U.S. Pat. No. 9,439,008, titled, "ONLINE HEARING AID FITTING SYSTEM AND METHODS FOR NON-EXPERT USER," all of which are incorporated herein by reference in their entirety for any purpose. This application is also related to U.S. patent application Ser. No. 14/683,946, titled, "SELF-FITTING OF A HEARING DEVICE," all of which applications are incorporated herein by reference, in their entirety, for any purpose.

TECHNICAL FIELD

Examples described herein relate to methods and systems of self-fitting of a hearing device, particularly for administration by a non-expert, including self-fitting by a consumer.

BACKGROUND

Current hearing aid fitting methods and instrumentations are generally costly and too complex for use by consumers and non-expert operators. The methods generally require administration by a hearing professional in a clinical setting. For example, an audiometer is typically required to produce an audiogram report, which forms the basis of hearing assessment and prescriptions in conventional fitting methods. Other instruments used may include a hearing aid analyzer, and a real-ear measurement (REM) instrument. A specialized sound-proof room, sometimes referred to as a sound room, is also generally required for conducting part or all of the fitting process. The fitting prescription from an audiogram report may be determined from a generic fitting formula, such as NAL or POGO, or from a proprietary formula, generally provided by the manufacturer of the hearing aid being fitted. The computations for the prescription are generally limited to hearing professional use, and the resultant prescriptions may vary considerably depending on the formula used, sometimes by as much as 20 decibels due to various factors including personal preferences.

Characterization and verification of a hearing aid prescription are generally conducted by presenting test sounds to the microphone of the hearing device, referred to herein generally as a microphonic or acoustic input. The hearing aid may be worn in the ear during the fitting process, for what is referred to as "real ear" measurements. Or it may be placed in a test chamber for characterization by a hearing aid analyzer. The stimulus used for testing is typically tonal sound but may be a speech spectrum noise or other speech-like signal such as "digital speech." Natural or real-life sounds are generally not employed in determination of a hearing aid prescription. Hearing aid users are generally asked to return to the clinic following real-life listening experiences to make the necessary adjustments. If real-life sounds are used in a clinical setting, a calibration procedure involving probe tube measurements with REM instruments is generally required. Regardless of the particular method used, conventional fittings generally require clinical settings to employ specialized instruments for administration by trained hearing professionals. The term "hearing aid," used herein, refers to all types of hearing enhancement devices, including medical devices prescribed for the hearing impaired, and personal sound amplification products (PSAP) generally not requiring a prescription or a medical waiver. The device type or "style" may be any of invisible in the canal (IIC), in-the-canal (ITC), in the ear (ITE), a receiver in the canal (RIC), or behind the ear (BTE). A canal hearing device refers herein to any device partially or fully inserted in the ear canal.

Programmable hearing aids generally rely on adjustments of the electroacoustic settings programmed within, referred to herein generally as "fitting parameters." Similar to hearing assessments and hearing aid prescriptions, the programming of a hearing aid generally requires specialized programming instruments and the intervention of a hearing professional to deal with complexities related to fitting parameters and programming thereof, particularly for an advanced programmable hearing aid, which may comprise over 15 adjustable parameters, and in some cases over 50 parameters.

For the aforementioned reasons among others, the fitting process for a programmable hearing device is generally not self-administered by the consumer. Instead, a licensed dispensing professional is typically involved for conducting at least one part of the fitting process, which may include hearing evaluation, hearing aid recommendation and selection, fitting prescription, fitting parameter adjustments and programming into the hearing device. This process often requires multiple visits to a dispensing office to incorporate the user's subjective listening experience after the initial fitting. Conventional fitting processes are generally too technical and cumbersome for self-administration, or for administration by a non-expert person. As a result, the cost of a professionally dispensed hearing aid, including clinician effort and the specialized instruments used in clinical settings, can easily reach thousands of dollars, and that cost is almost double for a pair of hearing aids. The high cost of hearing devices thus remains a major barrier preventing many potential consumers from acquiring a hearing aid, which typically costs under $100 to manufacture.

SUMMARY

A self-fitting system may include a hearing device and a computing device. The hearing device may include a speaker, memory, and wireless circuitry. The speaker may be configured to produce a test output representative of one or more test sound segments corresponding to predetermined suprathreshold loudness levels within an audible range of human hearing. The test output may be at least partially based on programmable fitting parameters of the hearing device.

The memory of the hearing device may be configured to store the one or more test sound segments and the programmable fitting parameters. A first set of programmable fitting parameters may be adjustable based on a consumer's assessment of a relatively loud level sound and a second set of programmable fitting parameters may be adjustable based on the consumer's assessment of a relatively soft level sound.

The wireless circuitry of the hearing device may be configured to receive a wireless command to produce the test output. The wireless circuitry may comprise wireless electronics and a wireless antenna. The hearing device may be configured to receive and execute wireless commands received by the wireless electronics to produce the test output.

The computing device may include a processing unit and wireless electronics. The processing unit may be configured to execute a fitting software application. The fitting software application may be configured to register the consumer's assessment of the test output. The wireless electronics of the computing device may be configured to transmit a wireless command to the hearing device. The wireless electronics of the computing device may be configured to wirelessly transmit one or more of the test sound segments to the hearing device.

BRIEF DESCRIPTION OF THE DRAWINGS

The above objectives, features, aspects and attendant advantages of the present invention will become apparent from the following detailed description of various embodiments, including the best mode presently contemplated of practicing the invention, when taken in conjunction with the accompanying drawings, in which.

DETAILED DESCRIPTION

Certain details are set forth below to provide a sufficient understanding of embodiments of the invention. Some embodiments, however, may not include all details described herein. In some instances, some well-known structures may not be shown, in order to avoid unnecessarily obscuring the described embodiments of the invention.

Figure 1:
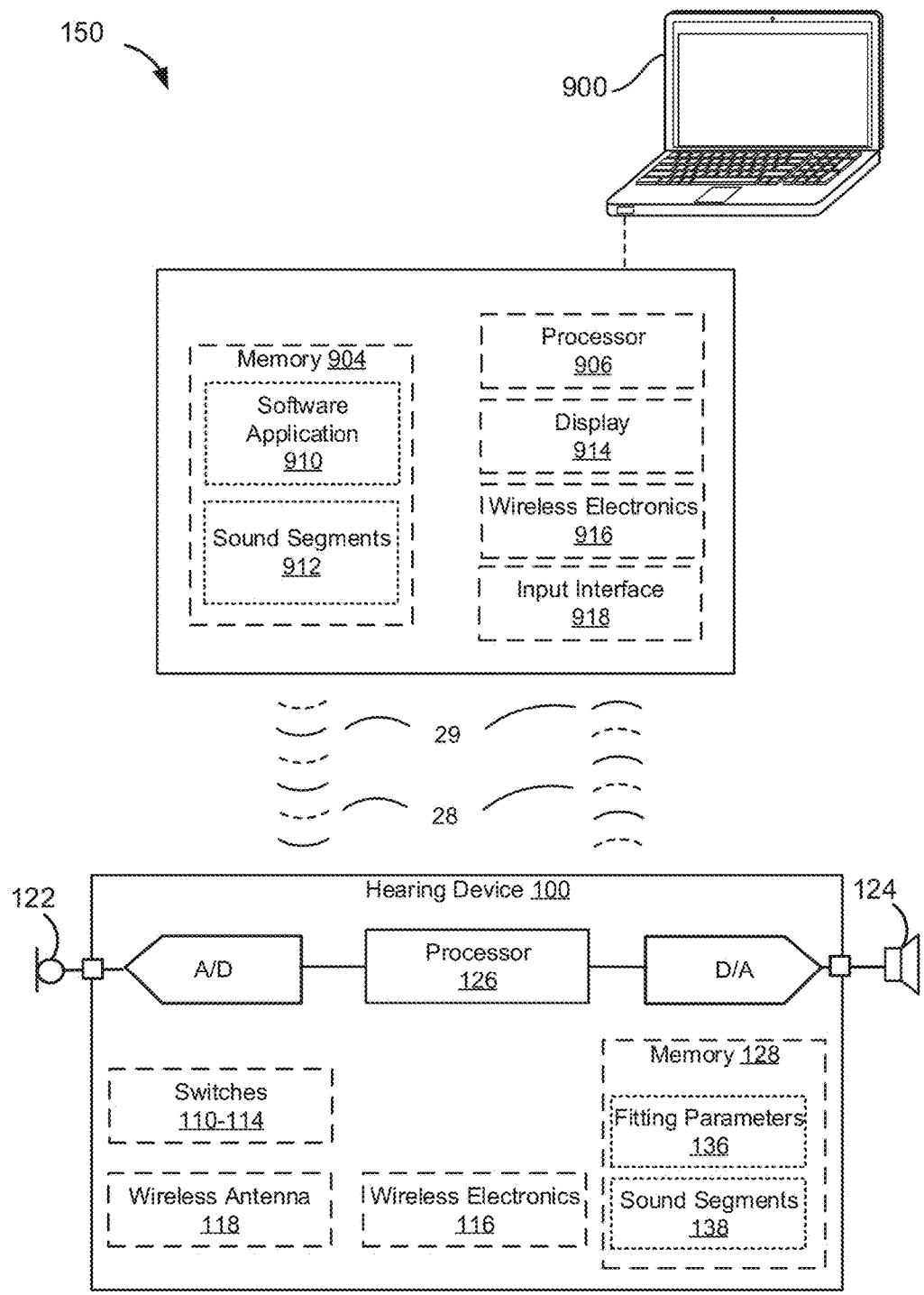
FIG. 1 is a representation of a self-fitting system for a programmable hearing device, according to some examples.

The present disclosure describes example systems and methods, as shown in FIGS. 1-12, for self-fitting of a hearing device by a non-expert consumer without resorting to clinical settings, and particularly suited for self-fitting by a hearing device consumer 1. Referring to FIG. 1, the self-fitting system 150 may include a programmable hearing device 100 for transmitting a test output 55 representative of one or more test sound segments 30 to an ear 2 of the consumer 1. The test sound segments 30 may be stored in memory 904 of a computing device 900 (e.g., sound segments 912) or in memory 128 of the hearing device 100 (e.g., sound segments 138). The test output 55 may be produced by a speaker 124 of the wireless hearing device 100. The test sound segments 30 may correspond to predetermined suprathreshold loudness levels within an audible range of human hearing. The test output 55 may be at least partially based on programmable fitting parameters 136 of the hearing device 100. The programmable fitting parameters 136 may be stored in memory 128 of the hearing device 100. A first set of programmable fitting parameters 136 may be adjustable based on the consumer's assessment of a relatively loud level sound and a second set of programmable fitting parameters 136 may be adjustable based on the consumer's assessment of a relatively soft level sound. In some embodiments, part or all of the sound segments 30 (also referred to herein as "digital audio files", "test audio segments," "test sound segments," and "audio segments") are obtained from natural sound recordings such as speech and environmental sounds, with each test sound segment (S1-S8 for example) comprising a unique combination of a sound level and frequency characteristics. The hearing device 100 may include wireless electronics 116 and a wireless antenna 118 for receiving a wireless command to produce the test output 55, adjust fitting parameters 136, or store sound segments 138.

Figure 2:
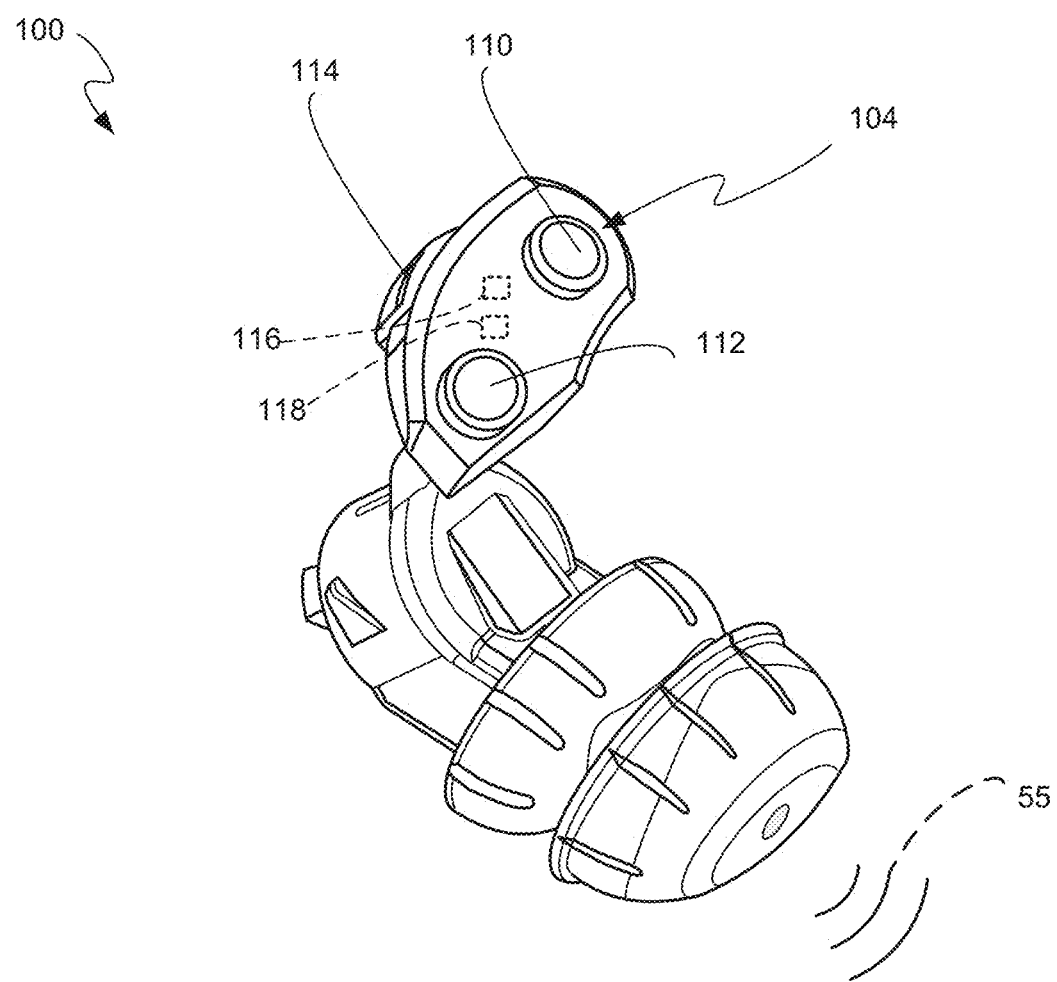
FIG. 2 is a view of a programmable hearing device including wireless circuitry, according to some examples.

The hearing device 100 may be provided in different configurations, including behind-the-ear (BTE), receiver-in-canal (RIC), in-the-ear (ITE), completely-in-canal (CIC), or any other known configuration. In some examples, as shown in FIGS. 1-2, the hearing device 100 may include durable components, such as a microphone 122, a speaker 124, wireless electronics 116, a wireless antenna 118, and sound processing circuitry 126. The hearing device 100 may be configured for positioning on or in the ear 2. The hearing device 100 may include a memory 128, for example non-volatile memory. The memory 128 may store one or more test sound segments 138, as described herein. The hearing device 100 may incorporate a rechargeable battery cell or a primary battery cell therein. In some examples, the hearing device 100 may be an integrated assembly or may be modular. The speaker 124 of the hearing device 100 may be configured to transmit sounds, for example test output 55, into the ear canal 14 of a user 100.

In some examples, the hearing device 100 may include wireless electronics 116 and/or a wireless antenna 118 (collectively referred to as "wireless circuitry"). The wireless antenna 118 may be positioned on a lateral end of the hearing device 100. The wireless circuitry may be operable to connect to a network via gateway device. The gateway device may be a computing device 900, a router or a node of a mesh network. In some examples, the hearing device 100 may include switches 110-114 for manual activation. Activation of any of the switches 110-114 may initiate or perform a wireless service by or for the hearing device 100. The wireless service may include performing self-fitting of the hearing device 100, controlling of an appliance, or conducting telephony functions. In some examples, the hearing device 100 may include a handle portion 104 housing the wireless circuitry and switches 110-114.

In some examples, the self-fitting system 150 may include a computing device 900 configured to communicatively couple to the hearing device 100, as shown in FIG. 1. The computing device 900 may be a client computer, a smartphone, a tablet, a portable media device, or any other device capable of executing computer instructions at a client side. The computing device 900 includes a processor 906 and memory 904 for storing executable instructions. The computing device 900 may be configured to execute the instructions to perform functions as described herein. The instructions may include instructions for executing one or more software applications, e.g., software application 910. The computing device 900 may include wireless electronics 916 for communications using a wireless interface (e.g., Bluetooth), for example to transmit wireless commands and/or sound segments 30 to the hearing device 100. In some examples, the computing device 900 may be connected to a network, for example the Internet, to access a remote server and web services. In some examples, the computing device 900 may store sound segment data 912 representative of sound segments 30 in the memory 904. In some examples, the computing device 900 may include a display 914 for presenting a user interface (e.g., desktop UI 19 or mobile UI 17) associated with the self-fitting system 150. In some examples, the computing device 900 may include an input interface 918, for example a keyboard, a mouse, or a touchscreen, for receiving user input indicative of a consumer's assessment of a test output 55. In some examples, the computing device 900 may transmit a wireless command to the hearing device 100 to play one or more sound segments 30 in response to the consumer's assessment of the test output 55. The computing device 900 may transmit a wireless command to adjust fitting parameters 136 and/or to produce a test output 55 representative of a sound segment 30 in response to a consumer input.

Figure 4:
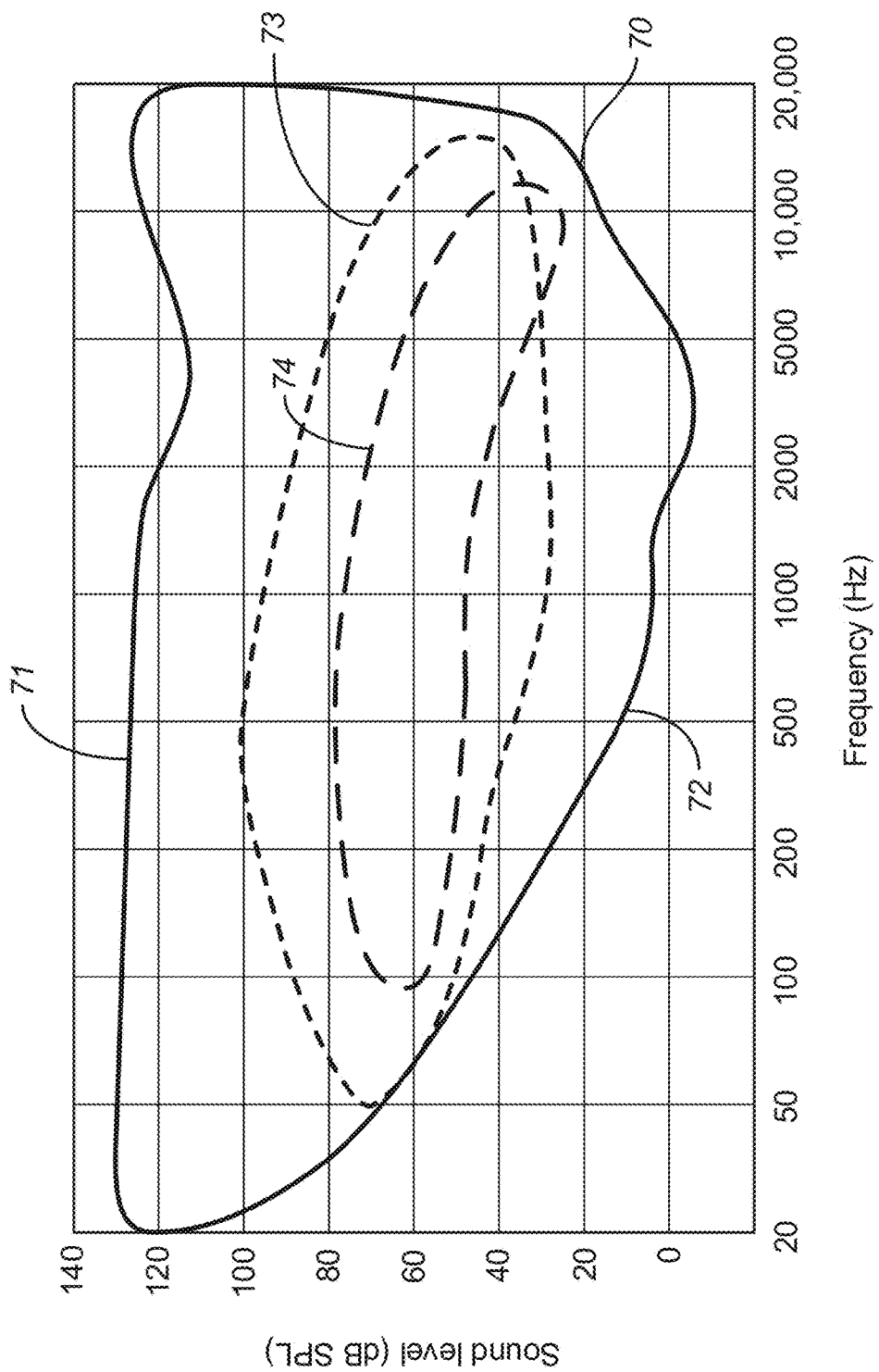
FIG. 4 is an example spectral graph depicting the human auditory range and the music and vocal ranges within the human auditory range.

FIG. 4 shows a spectral plot of the human auditory range generally spanning the frequencies between 20 to 20,000 Hz, and sound pressure between 0 dB to 130 dB SPL. Sounds naturally made, as well as certain audible man-made sounds, are considered herein as part of the auditory soundscape 70. The upper end 71 of the auditory soundscape generally refers to the threshold of pain, while the lower end 72 refers to the threshold of hearing. The musical range 73 and normal conversation (vocal) range 74 are also shown for reference and are generally well within the auditory soundscape 70.

Figure 5:
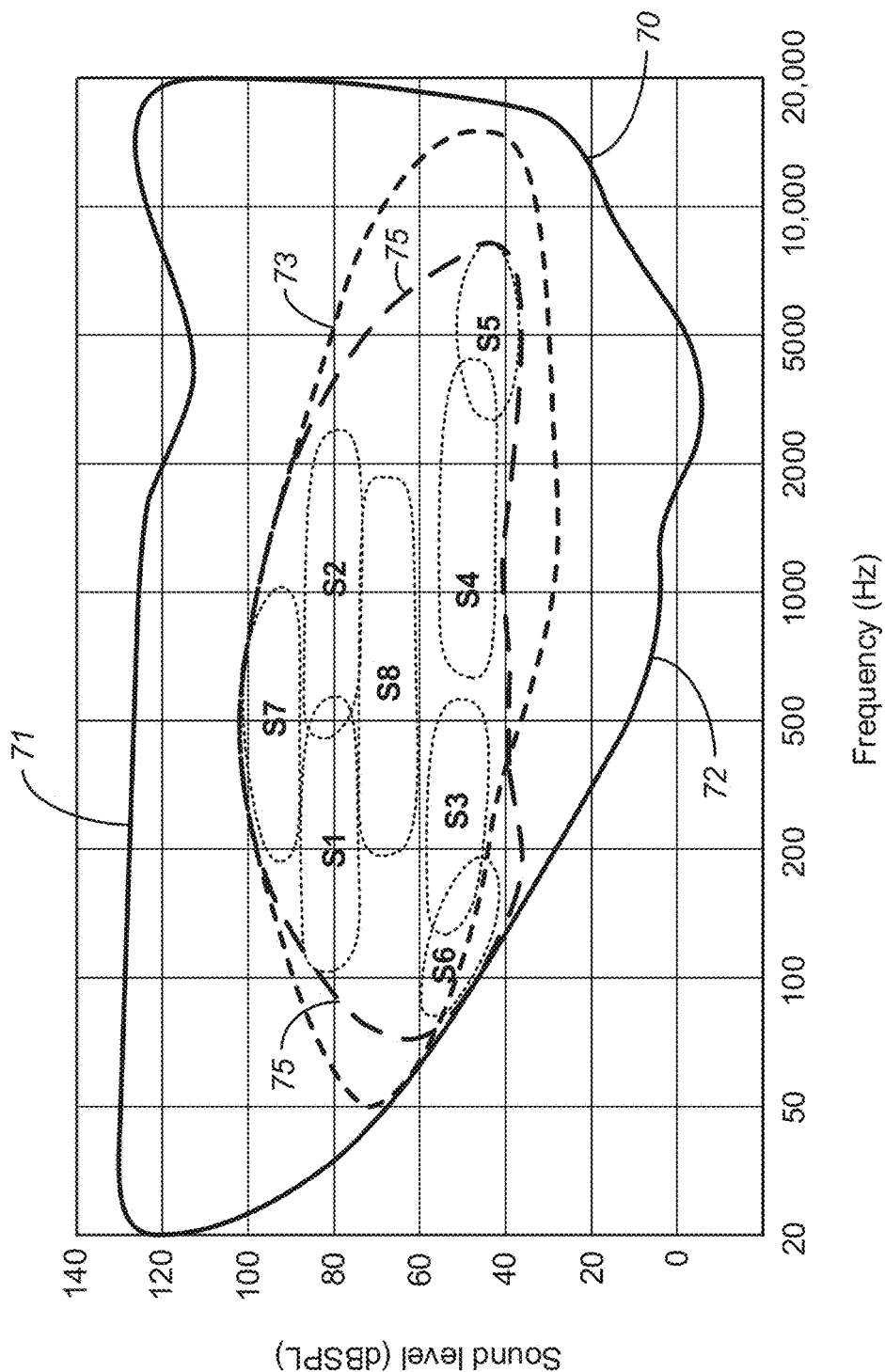
FIG. 5 is an example spectral graph of a fitting soundscape and test sound segments within.

Another aspect of the disclosure is the concept of a fitting soundscape 75 (FIG. 5) encompassing the spectrum of test sound segments 30 (S1-S8) having varied corresponding sound levels 40 and frequency characteristics for evaluating and determining effective communications in daily listening situations, and employed for conducting the fitting process according to the disclosures herein. The sound segments 30 (FIG. 8) may have spectral characteristic within the fitting soundscape 75. The sound segments 30 may include one or more sound segments corresponding to relatively low sound level, for example sound segments S3-S6, which are generally along the lower perimeter of the fitting soundscape 75, one or more sound segments corresponding to relatively loud sound level, for example sound segments S1, S2 and S7, which are generally along the upper perimeter of the fitting soundscape 75, one or more sound segments corresponding to relatively low frequency, for example sound segments S1, S3 and S6, and one or more sound segments corresponding to relatively high frequency, for example sound segments S2, S4 and S5). The sound segments 30 within the fitting soundscape 75 are generally at suprathreshold level, with respect to threshold of hearing 72 of normal hearing as shown in FIG. 5, and preferably comprise at least two speech segments (for example any of S1-S4) and at least one environmental sound segment (for example any of S6 and S7). The sound segments 30 are generally stored in digital format, for example as digital audio files. In one embodiment, the levels of test speech sound segments are at least 20 dB above the threshold of normal hearing 72. For reference purposes, it should understood that a 0 dB HL (hearing level) represents the threshold of hearing 72 for normal hearing individuals, and "suprathreshold" refers to sound levels above the threshold of hearing 72. It is also to be understood that the sound pressure level (SPL) at the threshold of hearing 72 for normal hearing individuals varies depending on the frequency, defining a different SPL for 0 dB HL reference at each frequency.

In one embodiment, sound segments corresponding to speech at relatively soft sound levels may include sound segments at sound levels within the range of 40-55 dB SPL. In some embodiments, sound segments corresponding to speech at relatively loud sound levels may include sound segments at sound levels within the range of 75-85 dB SPL. In some embodiments, a sound segment corresponding to environmental sound at a very loud sound level may include a sound segment at a sound level of approximately 90 dB SPL. In some embodiments, sound segments corresponding to a relatively soft background sound, such as fan noise, may include sound segments at sound levels within the range of 30-45 dB SPL. In some embodiments, sound segments corresponding to broad band environmental sounds, such as music or TV sounds, may include sound segments at sound levels within the range of 60-70 dB SPL. The latter sound segments may be used for final level adjustment or balance adjustments across a pair of hearing devices during a binaural fitting.

Systems for providing realistic listening scenarios by acoustically coupling sound from a speaker to the microphone of the hearing device are known in the art. In addition to requiring an external speaker, these known fitting methods typically involve a REM incorporating calibrated probe tube microphones. To provide realistic listening scenarios, some of these systems rely on a complex setup to measure individual head related transfer function. Thus, these known systems and methods are generally limited to clinical and research settings.

Figure 8:
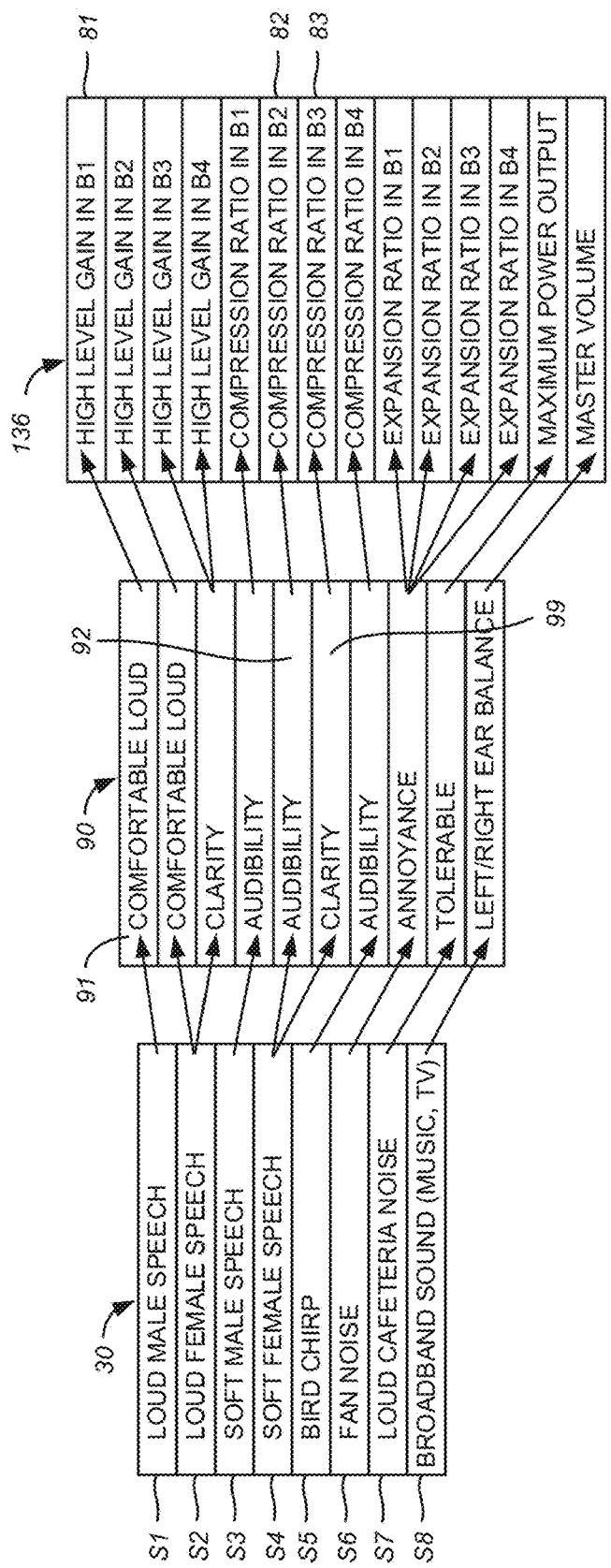
FIG. 8 depicts multiple test sound segments and their assignment to corresponding consumer controls and fitting parameters of a programmable hearing device, according to some examples.
Figure 9:
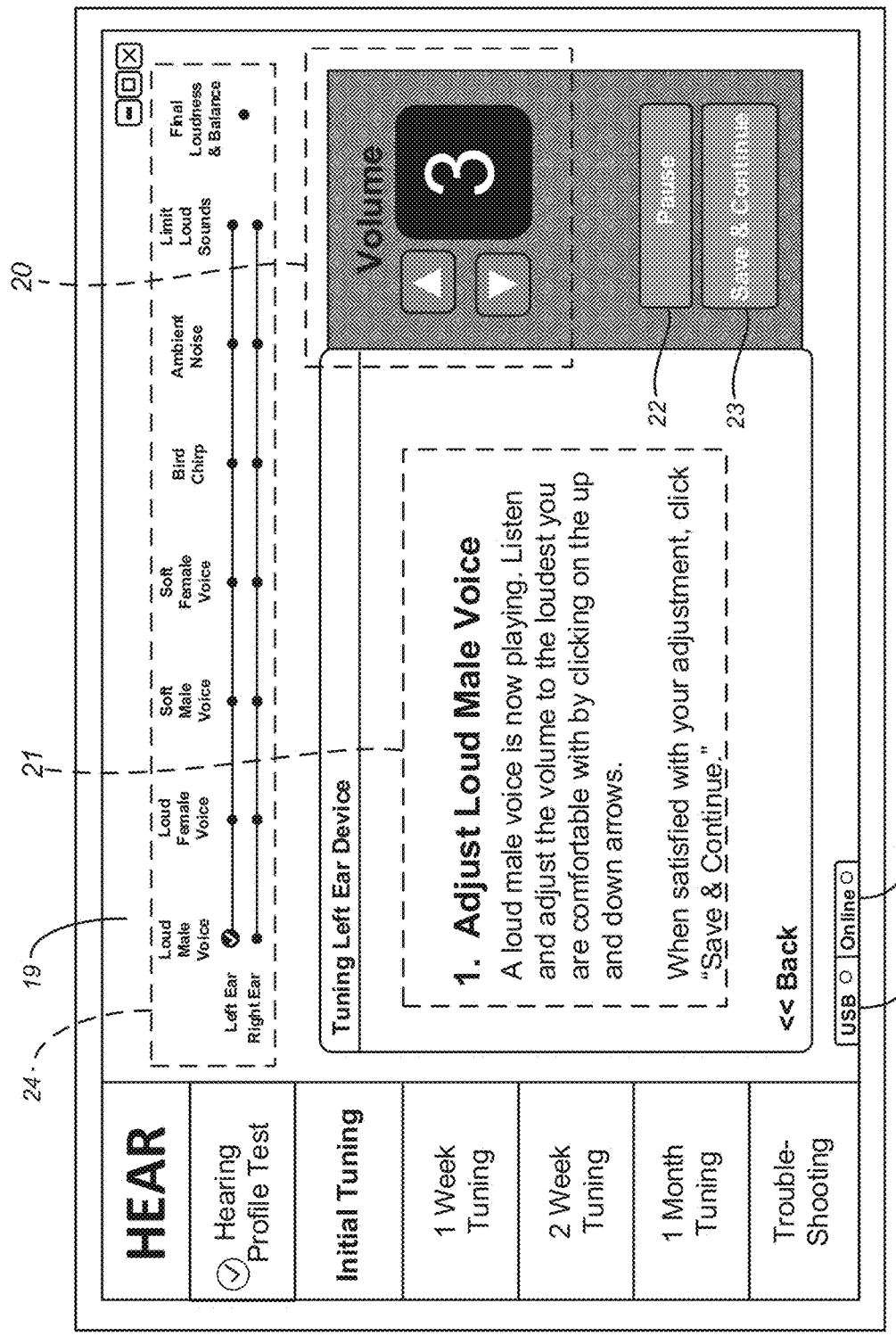
FIG. 9 is a representation of a user interface (UI) of a self-fitting system to adjust loudness and corresponding high-level gain in the low frequency band of signal processing of a hearing device communicatively coupled to a computing device, during a presentation of the loud male speech, wherein the UI also shows instructions and indicators for a non-expert user, according to some examples.

Referring to FIG. 9, one embodiment of the fitting method generally involves instructing a hearing device consumer 1 to listen to a test output 55 of the in-situ programmable hearing device 100 communicatively coupled to a computing device 900. The consumer 1 may be presented with a user interface 19 on the computing device 900 with controls 20 (FIG. 9) to adjust and program corresponding programmable fitting parameters 136 (FIG. 8), while subjectively evaluating the test output 55 corresponding to sound segments 30 (FIG. 8). The test output 55 may correspond to sound segments 30 presented at suprathreshold levels. In some examples, the computing device 900 may deliver sound segment data 912 to the hearing device 100 using wireless electronics 916 for storage in memory 128 of the hearing device 100 or playback using the speaker 124 of the hearing device 100. The sound segment data 912 may be used to generate the sound segments 30 which are provided to the user as test output 55. As the consumer 1 is listening to the test output 55, the consumer may evaluate the test output. A user (e.g., the consumer 1, or a person assisting the consumer 1) may submit user input to the system (e.g., an evaluation of the test output 55) using an input interface 918 of the computing device 900, such as a keyboard, a mouse, or a touchscreen. The computing device 900 may register the consumer's assessment of the test output 55 for adjustment and programming of the corresponding programmable fitting parameters 136.

Figure 6:
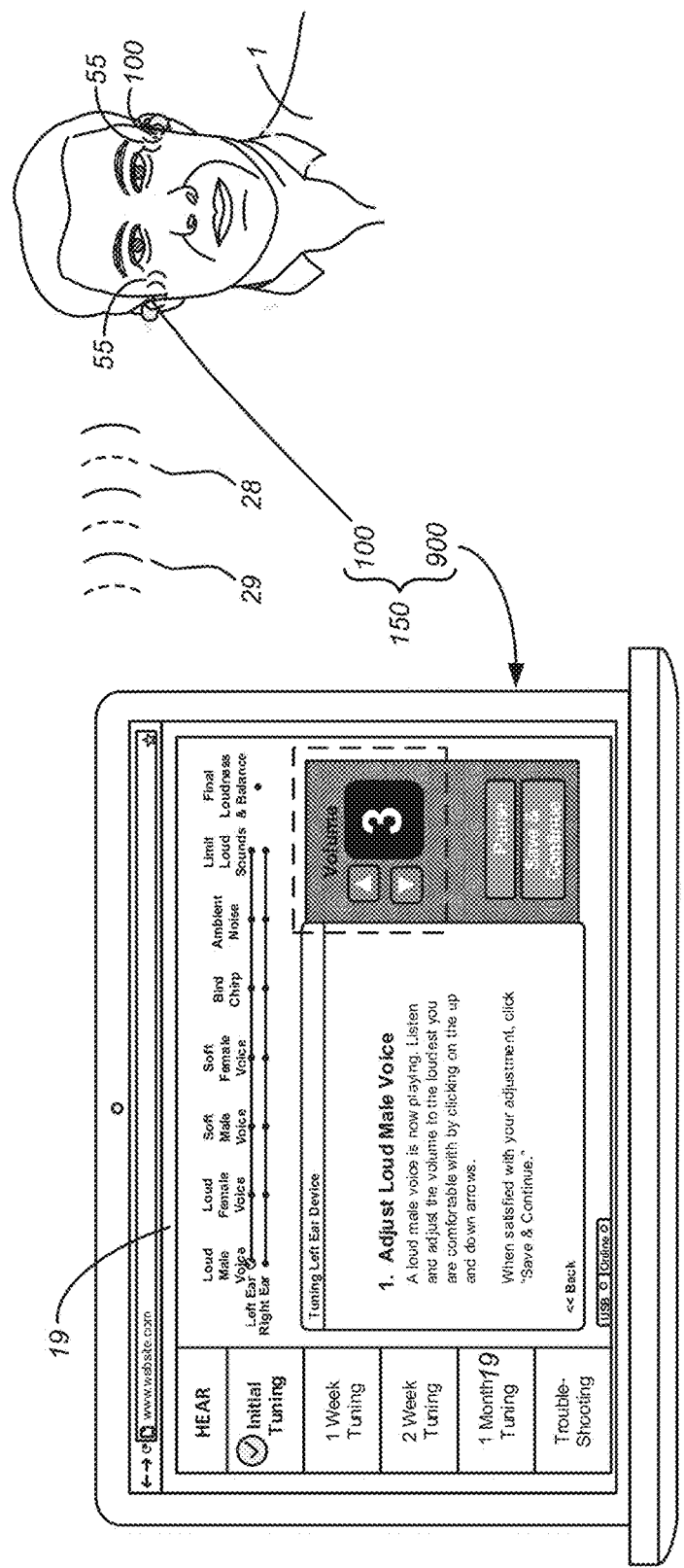
FIG. 6 is a representation of a self-fitting system, including a computing device for generating test audio signals and programming signals, and a programmable hearing device in-situ for receiving test audio signals, according to some examples.
Figure 7:
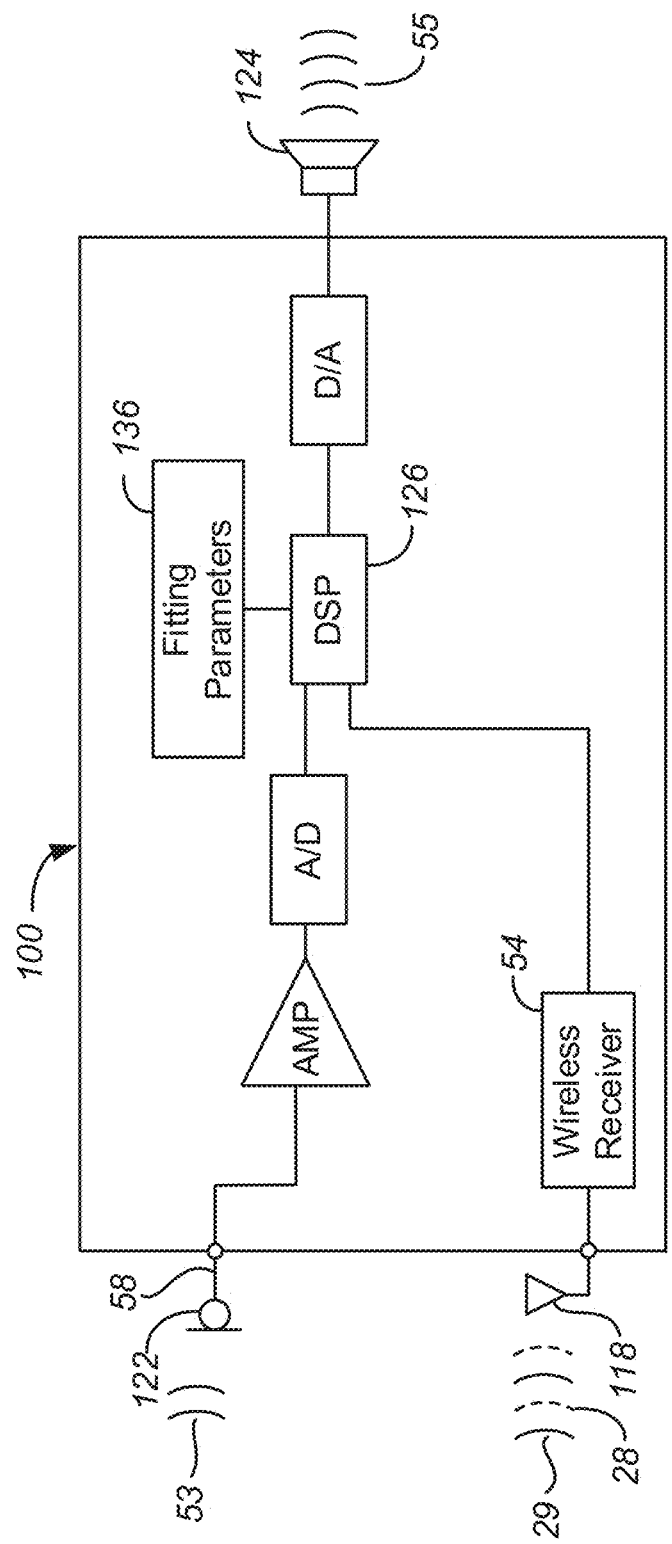
FIG. 7 is a representation of a programmable hearing device, showing multiple audio input options, including a microphone (acoustic) input and a non-acoustic input, to implement the fitting method disclosed herein, according to some examples.

In one embodiment, as shown in FIG. 6, the fitting system 150 includes a computing device 900 with memory 904 storing a fitting software application 910 for execution by a processor 906 of the computing device 900. The computing device 900 may be configured to store sound segments 912 in memory 904, and transmit the sound segments 912 as files or audio streamed by the computing device 900 to the programmable hearing device 100 in-situ. For reference purposes, as shown in the block diagram of the programmable hearing device 100 (FIG. 7), an acoustic or microphonic input generally refers to any signal associated with the microphone 122 of the hearing device 100, including the electrical signal 58 generated from the microphone 122, or the test sound 53 presented thereto. Referring to FIG. 7, the example hearing device 100 may include a digital signal processor (DSP) 126 and a speaker 124 for generating the test output 55. The hearing device audio inputs may be acoustic such as 53 or 58 or wireless, for example wireless antenna 118, in conjunction with wireless electronics 116 for receiving wireless audio signals 28 and wireless programming signals 29. Alternative hearing device input options are shown co-existing in FIG. 7 but it should be understood that they may not all co-exist in a typical hearing device application, or for implementing the teachings of the present disclosures.

In some examples, as shown in FIGS. 4 and 7, the computing device 900 may be configured to generate and transmit programming signals 29 to the programmable hearing device 100 in-situ. In some examples, consumer controls 20 (FIG. 8) for adjusting fitting parameters 136 are offered by the fitting software application 910 to the consumer 1 for subjective assessment and selection generally in lay terms, such as loudness, audibility, clarity, etc., rather than technical terms and controls conventionally offered to hearing professionals such as gain, compression ratio, expansion ratio, etc.

To mitigate the effects of room noise in certain room environments, a microphone may be incorporated within the computing device 900 to sense sound present in the vicinity of the consumer 1. The self-fitting process may then be adjusted according to the noise condition. For example, the self-fitting process may be adjusted by delaying the presentation of test stimuli during a noise burst in the room, or by halting the self-fitting process in the presence of excessive noise.

Using various embodiments of the fitting system 150, consumers may interactively develop their own "prescriptions" and program the prescriptions into their programmable hearing devices. The prescriptions may be developed using the subjective assessment of a test output 55 rather than prescriptive formulae or specialized fitting instruments or relying on professionals and clinical settings. The wireless audio signal 28 may include an audio signal corresponding to a sound segment 30 generated by the fitting system 150 (e.g., the computing device 900) and transmitted to the hearing device 100 at a predetermined loudness level. The predetermined loudness level of audio signals eliminates calibration processes associated with delivering actual acoustic test sound 53 to the microphonic input of hearing devices. In some examples, the audio signals generated by the computing device 900 may be representative of sound segments 912 stored within memory 904 of the computing device 900. The wireless programming signal 29 may be transmitted from the fitting system 150 to the hearing device 100 to adjust fitting parameters 136. For example, the wireless programming signal 29 may be transmitted from the computing device 900 to the programmable hearing device 100 in response to a consumer's subjective assessment of a test output 55 to adjust one or more fitting parameters 136 associated with the test output 55. The consumer's subjective assessment may be received by an input interface 918, for example a mouse or touchscreen, of the computing device 100. The computing device 100 may present consumer controls 20 on a display 914 of the computing device 100 to prompt the consumer to input their subjective assessment of the test output 55. In some examples, the wireless programming signal 29 may include a wireless command to produce the test output 55 based on one or more test sound segments 138 stored in memory 128 of the programmable hearing device 100. The programmable hearing device 100 may produce the test output 55 using programmable fitting parameters 136 stored within the memory 128. The wireless command may include instructions to produce one or more test outputs 55 representative of one or a sequence of test sound segments 138.

Figure 3:
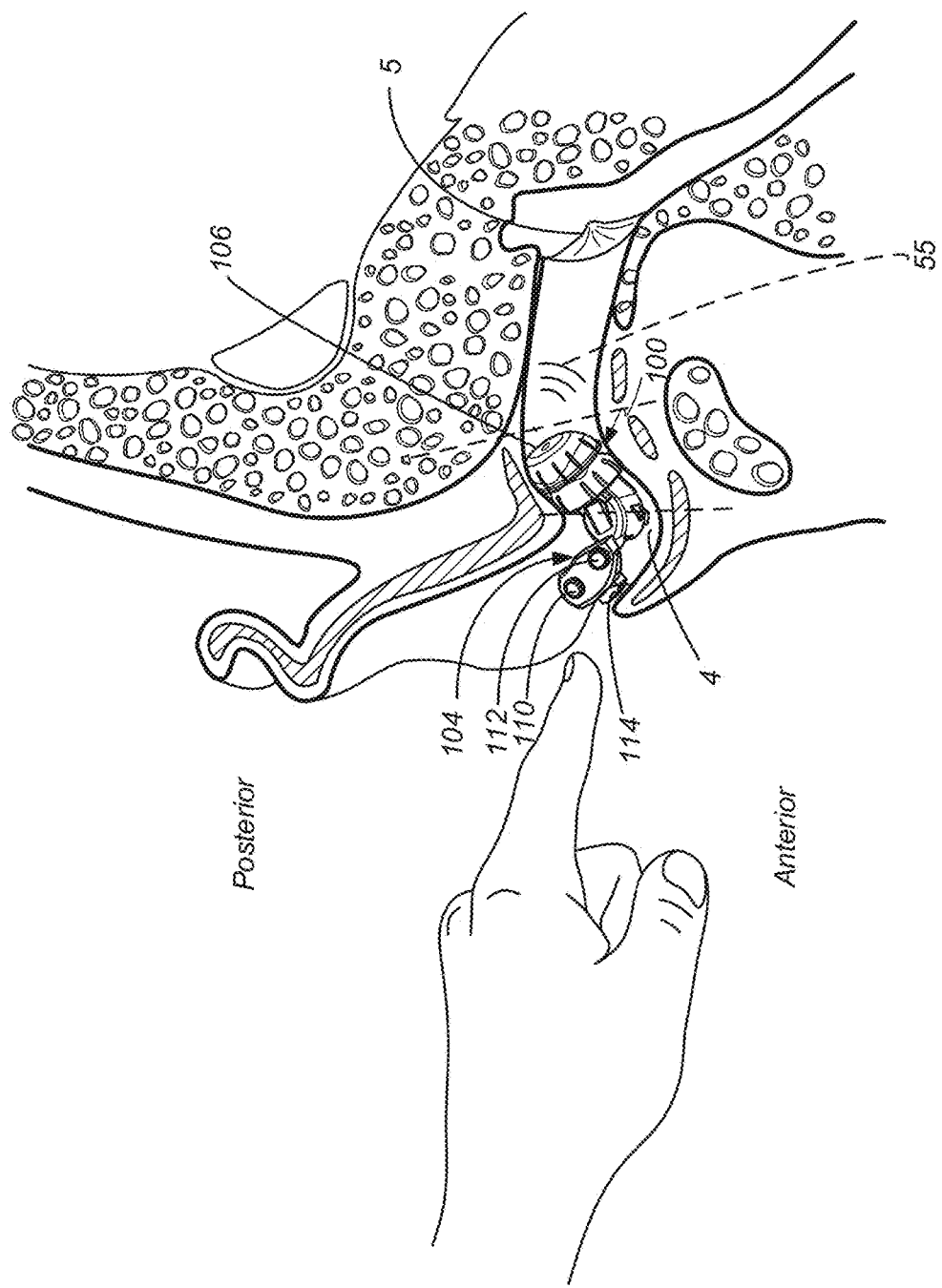
FIG. 3 is an illustration of a programmable hearing device positioned inside an ear canal, according to some examples.

The fitting system 150 may allow the consumer 1 to manipulate fitting parameters 136 stored within the memory 128 of the hearing device 100 using consumer controls 20, based on the subjective response to a test output 55 presented in the ear 2 to the ear drum 15 (FIG. 3). The consumer controls 20 may be provided on a user interface 19 (FIG. 9), and may receive input from a consumer 1 based on fitting controls 90 (FIG. 8) to determine adjustments to fitting parameters 136. The process of presenting test output 55 and programming according to the subjective assessment of the consumer 1 is repeated for a set of sound segments 30 until all corresponding fitting parameters 136 are adjusted according to the instructions provided to the consumer 1 for each sound segment 30. In some examples, the sound segments 30 are selected with minimal overlap in the combination of level and frequency characteristics, thus minimizing the overlap in parameter optimization and expediting the fitting process for administration by a non-expert user, including for self-administration. The consumer 1 may be presented with one or more consumer controls 20 corresponding to one or more fitting controls 90 associated with the sound segment 30 being presented. The fitting controls 90 may designate subjective criteria for consumer adjustments, such as comfortable loud 91, audibility 92, or clarity 99. Each fitting control 90 may be associated with one or more fitting parameters 136. Thus, each sound segment 30 may be related to one or more fitting parameters 136 via fitting controls 90. For example, loud male speech S1 may be associated with the comfortable loud 91, which is associated with high level gain in B1 81.

The fitting system 150 and method allows the dispensing of a hearing device and administering the fitting process at a non-clinical environment, such as in a home or an office. The hearing device may be delivered to the consumer's home, by mail for example. This "home fitting" aspect substantially reduces the cost of hearing device acquisition and eliminates hassles and inconvenience associated with multiple visits to professional settings. In some examples, the fitting process may be conducted locally with a fitting software application 910 stored in memory 904 of the computing device 900. In some examples, the fitting process may be conducted online, with a fitting software application hosted by a remote server for execution by the computing device 900 connected online to the remote server.

Another aspect of the present disclosure is to present real-life scenarios with a set of sound segments 30 selected specifically to expose the range of fitting parameters 136 within a hearing device 100 for their adjustment by a non-expert user using subjective assessment without clinical instrumentation. Natural sound recordings may be filtered by an audio processor application, for example Audacity® for Windows, to enhance and tailor the spectral characteristics of a natural sound recording to a corresponding set of fitting parameters. For example, a loud male speech segment S1 may be presented at a signal level corresponding to sound pressure level of approximately 80 dB SPL. A calibration constant associated with sound level calibration for each sound segment is stored in the memory of the fitting system 150. In some embodiments, relatively loud speech signals may be presented in the range of 75-85 dB SPL. For example, a loud male speech segment S1 may be present to allow a consumer 1 to adjust a high-level gain parameter 81 (FIG. 8) in the low frequency band range, referred to herein as B1. The original male speech recording may be filtered by the aforementioned audio processor application to enhance the low frequency spectral characteristics.

FIG. 9 shows an example user interface (UI) 19 for a fitting software application (e.g., software application 910) with loudness (Volume) control 20 provided to the consumer 1 to adjust the high-level gain parameter 81 of the hearing device 100 in B1. The UI 19 shows UI elements including user instructions 21, pause control 22, save control 23, fitting process status 24, online connection status 25, and programming connection status 26. In some examples, the subjective assessment of "Volume" (loudness) of a test output 55 with "Loud Male Voice" specifies gain fitting parameter 81 of the hearing device 100 corresponding to loudness in the low frequency band. The Loud Male Voice (e.g., sound segment S1) may be associated with a comfortable loud fitting control 91 (FIG. 8). The consumer 1 may use the volume control 20 to increase the loudness of the test output 55, using an up arrow, based on a subjective assessment that the test output 55 was not sufficiently loud. In another example, the consumer 1 may use a down arrow of volume control 20 to decrease the loudness of the test output 55 using, based on a subjective assessment that the test output 55 was uncomfortably loud. The subjective assessment of the consumer 1 is generally correlated to an adjustment of one or more fitting parameters 136, which may be interactively adjusted based on the assessment of the consumer 1. The computation for adjusting fitting parameters 136 (e.g., the correlation between the user input indicating the consumer's subjecting assessment and the fitting parameter to be adjusted) may be performed by a processor within the fitting system 150, for example a microprocessor within the computing device 900 or a remote server. For example, the subjective assessment of loudness of a "Loud Male Voice" may be correlated to an adjustment to a gain fitting parameter 81 corresponding to loudness in the low frequency band. Other examples, shown in the process status 24 of user interface 19 of FIG. 9, relate to other subjective aspects of audibility such as threshold of hearing audibility and clarity for "Soft Female Voice," annoyance of "Ambient Noise," and audibility of ultra high-frequency sound represented by a "Bird Chirp." Fitting parameters 136 associated with the subjective aspects of audibility may be adjusted based on a selection by the consumer 1 through a user interface (e.g., desktop UI 19 or mobile UI 17), similar to the adjustment of gain fitting parameters 81 associated with loudness perception described above. As further examples, the subjective assessment of loudness of a "Loud Female Voice" (e.g., sound segment S2) may be correlated to an adjustment to the same or another gain fitting parameter corresponding to loudness in the low frequency band, e.g., as shown in FIG. 8. The subjective assessment of clarity of a "Loud Female Voice" may be correlated to an adjustment to the same or yet another gain fitting parameter corresponding to loudness in the low frequency band. The subjective assessments of audibility of a "Soft Male Voice" (e.g., sound segment S3) or a "Soft Female Voice" (e.g., sound segment S4) may be correlated to an adjustment to one or more compression ratios, and so on for any subjective aspect of audibility such as those listed in FIG. 8. At each stage of the fitting process (e.g., as shown by process status 24), a consumer control 20 (one example of which is the loudness control 20 in FIG. 9) may be provided for each subjective aspect of audibility to be tested. Each user interface window associated with each stage of the fitting process (e.g., UI 19, or UI 17 in FIG. 10) may be similarly configured to include one or more similar components to the example user interfaces in FIGS. 9 and 10, such as instructions 21, pause control 22, save control 23, fitting process status 24, online connection status 25, and programming connection status 26, along with the appropriate fitting control for the particular stage of the fitting process. In some examples, multiple fitting controls (e.g., adjust controls 14 and 15) may be associated with a given fitting stage and thus presented for receiving the consumer's subjective assessment of a given sound segment.

In some examples, the fitting software application 910 may be standalone or browser-based. The fitting software application 910 may provide access to and control of the hearing device 100. The computing device 900 may include memory 904 to store components of the fitting software application 910, such as sound segment data 912 representative of test sound segments 30, calibration constants, test results, user information, etc. In some examples, the hearing device 100 may store one or more sound segment data 138 representative of test sound segments 30 in its local memory 128. The hearing device 100 may wirelessly receive one or more test sound segments 30. When receiving sound segment data representative of a test sound segment 30, the hearing device 100 may determine a free space level of the memory 128. When a file size of the sound segment data exceeds the free space level of the memory 128, the hearing device 100 may erase previously stored sound segment data representative of one or more test sound segments 30. The sound segments data may be received in real time for live streaming or received at a faster or slower rate for non-real time playback by the hearing device 100. In some examples, it may be advantageous to utilize non-real time playback to minimize battery consumption and/or load times.

Figure 10:
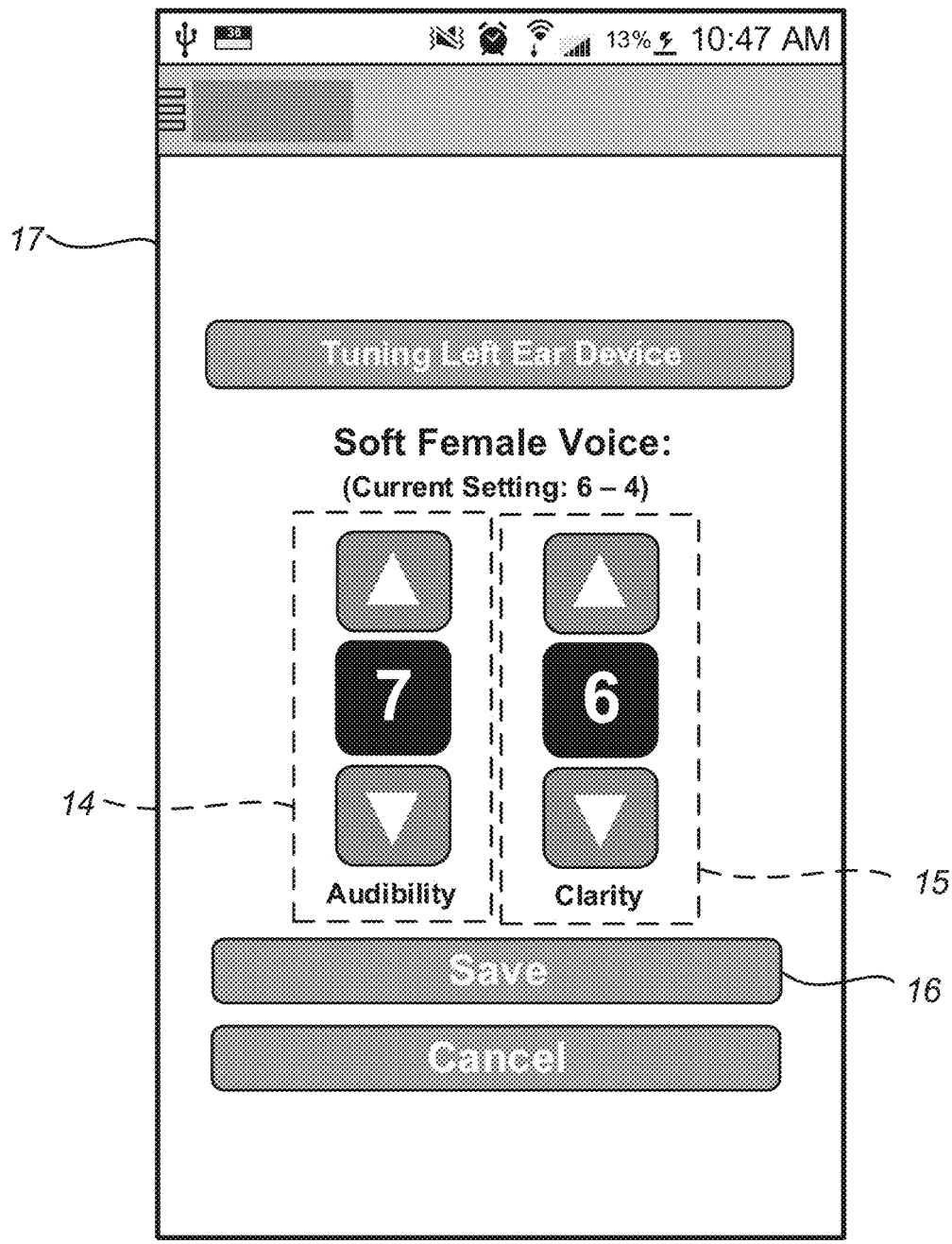
FIG. 10 is a representation of a user interface (UI) for a smartphone of a self-fitting system to adjust multiple controls corresponding to multiple fitting parameters of a hearing device during the presentation of the soft female speech, wherein the UI shows audibility control, clarity control and indicators, according to some examples.
Figure 11:
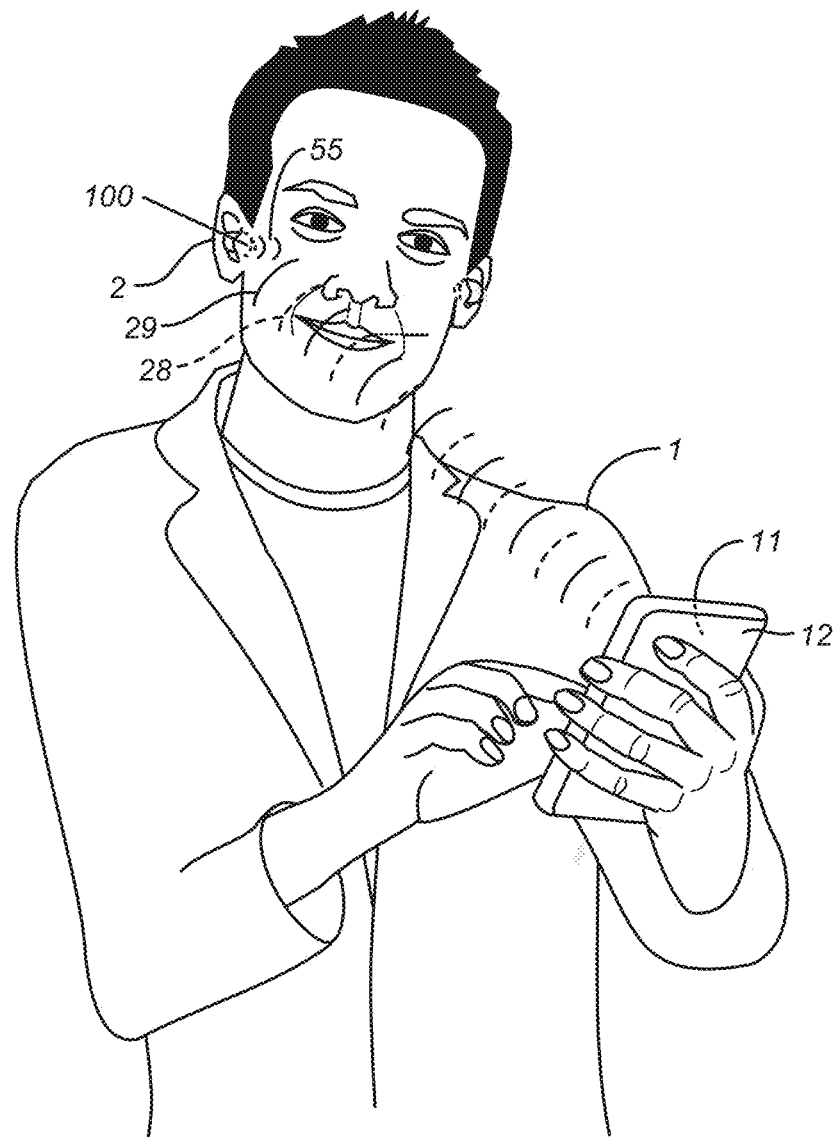
FIG. 11 is a perspective view of a wireless implementation of the self-fitting system using a smartphone executing a fitting application, wherein the system is configured to transmit a wireless programming signal and a wireless test audio signal to the programmable hearing device in-situ, according to some examples.

FIG. 10 shows an example user interface (UI) 17 for a smartphone fitting application to adjust fitting parameters 82 and 83, associated with soft female speech. UI 17 may include UI elements such as consumer controls which may be associated with one or more subjective aspect of audibility. The consumer controls may include audibility control 14 and clarity control 15. The UI 17 may also include other controls such as save function control 16. The consumer 1 may be instructed to listen to a soft female sound, and adjust controls 14 and 15 on the touch screen 11 (FIG. 11) of the smartphone 12, according to the listening experience of the consumer 1 from the in-situ test output 55. In various embodiments, other fitting parameters 136 may be adjusted in a substantially similar manner using the user's subjective response to the test output 55 in-situ. FIG. 11 shows a wireless embodiment of the fitting system 150, whereby wireless audio signals 28 and wireless programming signals 29 are wirelessly transmitted from the smartphone to implement the aforementioned teachings of the fitting process in conjunction with the programmable hearing device 100. The fitting system and interactive methods disclosed herein enable self-fitting for a consumer 1 with minimal computer skills, or by a non-expert person assisting the consumer 1.

Figure 12:
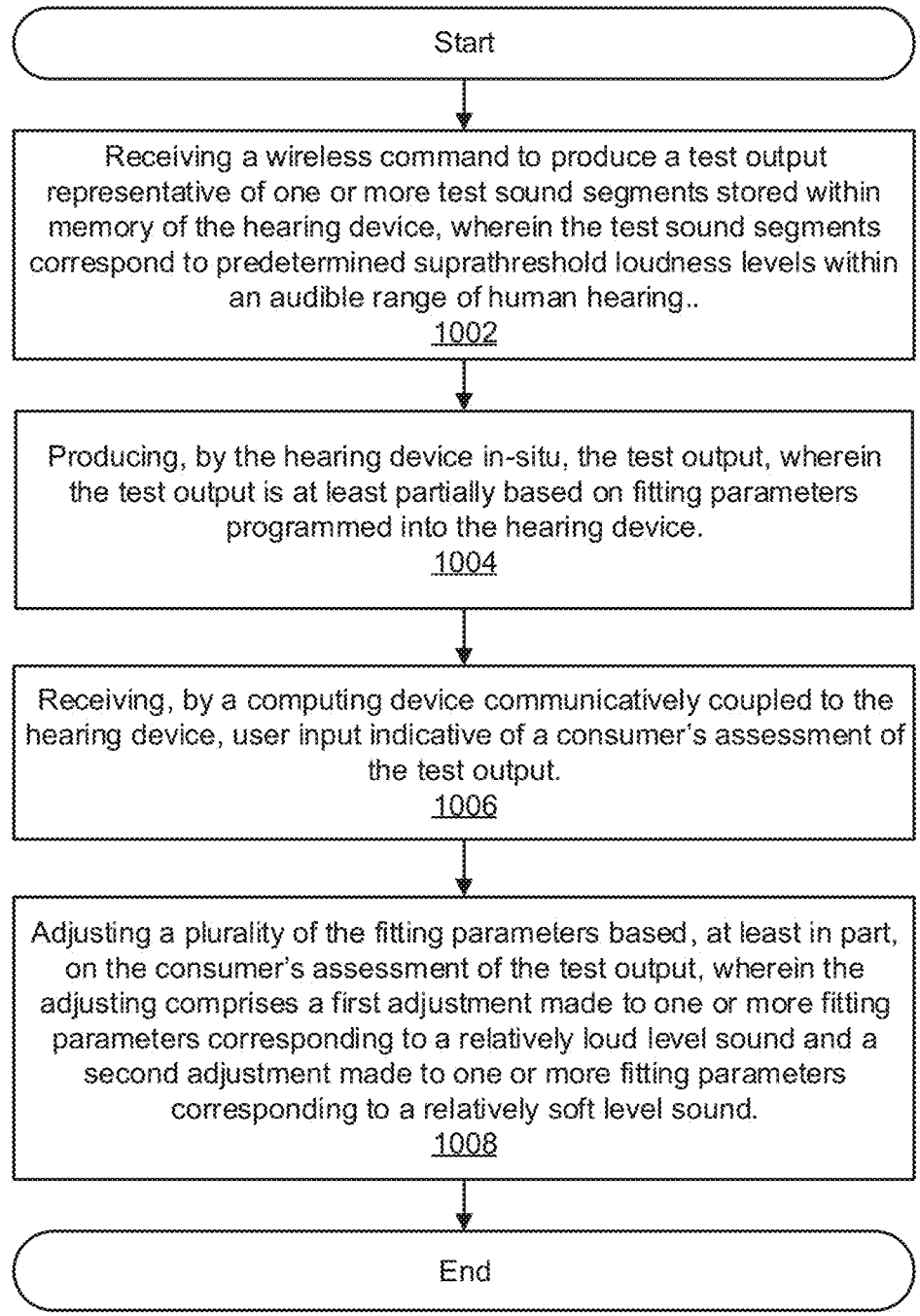
FIG. 12 is a flow chart for self-fitting of a hearing device, according to some examples.

FIG. 12 is a flow chart representation for self-fitting a hearing device for a consumer, according to some examples. While the various steps in these flowcharts are presented and described sequentially, one of ordinary skill will appreciate that some or all of the steps can be executed in different orders and some or all of the steps can be executed in parallel. Further, in one or more embodiments, one or more of the steps described below can be omitted, repeated, and/or performed in a different order. Accordingly, the specific arrangement of steps shown in FIG. 12 should not be construed as limiting the scope of the invention.

FIG. 12 is a flow chart representation for a method, according to some examples. In step 1002, a wireless command is received to produce a test output representative of one or more test sound segments stored within memory of the hearing device, wherein the test sound segments correspond to predetermined suprathreshold loudness levels within an audible range of human hearing. In step 1004, the test output is produced by the hearing device in-situ, wherein the test output is at least partially based on fitting parameters programmed into the hearing device. In step 1006, user input indicative of a consumer's assessment of the test output is received by a computing device communicatively coupled to the hearing device. In step 1008, a plurality of the fitting parameters are adjusted based, at least in part, on the consumer's assessment of the test output, wherein the adjusting comprises making a first adjustment to one or more fitting parameters corresponding to a relatively loud level sound and making a second adjustment to one or more fitting parameters corresponding to a relatively soft level sound.

Although examples of the invention have been described herein, variations and modifications of this exemplary embodiment and method may be made without departing from the true spirit and scope of the invention. Thus, the above-described embodiments of the invention should not be viewed as exhaustive or as limiting the invention to the precise configurations or techniques disclosed. Rather, it is intended that the invention shall be limited only by the appended claims and the rules and principles of applicable law.

What is claimed is:

1. A hearing device comprising: a speaker configured to produce a test output representative of one or more test sound segments corresponding to suprathreshold loudness levels within an audible range of human hearing, wherein the test output is at least partially based on programmable fitting parameters of the hearing device; memory configured to store test sound segments representative of a loud level sound and a soft level sound, and the programmable fitting parameters, wherein a first set of programmable fitting parameters are adjustable based on a consumer's assessment of the loud level sound and a second set of programmable fitting parameters are adjustable based on the consumer's assessment of the soft level sound, and wireless circuitry configured to receive a wireless command to produce the test output, wherein the wireless command is configured to cause the hearing device to produce a test output representative of the test sound segments stored in the memory.

2. The hearing device of claim 1, wherein the wireless circuitry comprises a wireless antenna positioned on a lateral end of the hearing device.

3. The hearing device of claim 1, further comprising a processing unit configured to receive and execute the wireless commands received by the wireless circuitry to produce the test output.

4. The hearing device of claim 1, wherein the wireless circuitry is configured to receive programming signals to adjust one or more programmable fitting parameters.

5. The hearing device of claim 1, wherein at least one of the test sound segments is representative of speech.

6. A self-fitting system comprising: a hearing device comprising: a speaker configured to produce a test output representative of one or more test sound segments corresponding to suprathreshold loudness levels within an audible range of human hearing, wherein the test output is at least partially based on programmable fitting parameters of the hearing device; a memory storing the one or more test sound segments and the programmable fitting parameters, wherein the one or more test sound segments are representative of a loud sound and a soft sound, and wherein a first set of programmable fitting parameters are adjustable based on a consumer's assessment of the loud level sound and a second set of programmable fitting parameters are adjustable based on the consumer's assessment of the soft level sound; and wireless circuitry configured to receive a wireless command to produce the test output; and a computing device comprising: a processing unit configured to provide a user interface, wherein the user interface is configured for receiving user inputs indicative of the consumer's assessments of the test output, wherein the processing unit is further configured to determine adjustments to the programmable fitting parameters based on the user inputs and generate a wireless command comprising the adjustments; and wireless electronics configured to transmit the wireless command to the hearing device, wherein the hearing device is configured to execute the wireless command to adjust the programmable fitting parameters while the test output is being produced by the speaker.

7. The hearing device fitting system of claim 6, wherein the computing device is configured to display a consumer control for receiving the user inputs, and wherein the processing unit is configured to determine adjustments to programmable fitting parameters of the hearing device associated with the loud level sound and the soft level sound based on the user inputs.

8. The hearing device fitting system of claim 6, wherein the computing device is configured to wirelessly transmit one or more of the test sound segments to the hearing device, wherein the wireless command comprises instructions to produce a test output representative of at least one of the wirelessly transmitted test sound segments.

9. A method of self-fitting a hearing device for a consumer, the method comprising: providing a hearing device comprising memory storing test sound segments representative of a loud sound and a soft sound; producing, by the hearing device in-situ, a test output representative of one or more test sound segments, wherein the test output is at least partially based on fitting parameters programmed into the hearing device, and wherein the test sound segments correspond to suprathreshold loudness levels within an audible range of human hearing; and adjusting a plurality of the fitting parameters based, at least in part, on the consumer's assessment of the test output, wherein the adjusting comprises making a first adjustment to one or more fitting parameters corresponding to the loud level sound by a computing device and making a second adjustment to one or more fitting parameters corresponding to the soft level sound by the computing device.

10. The method of claim 9, further comprising receiving, by the hearing device, a wireless command to produce one or more test outputs.

11. The method of claim 9, further comprising receiving, by the hearing device, one or more test sound segments and storing the one or more test sound segments in the memory of the hearing device.

12. The method of claim 11, further comprising determining a free space level of the memory.

13. The method of claim 12, further comprising erasing one or more test sound segments stored in memory when a file size of the one or more test sound segments received exceeds the free space level.

14. The method of claim 9, further comprising providing fitting controls for receiving the consumer's assessment through a user interface of the computing device.

15. The method of claim 14, further comprising receiving the consumer's assessment via the fitting controls.

16. The method of claim 15, wherein the consumer's assessment of the test output is received by a mouse, keyboard, or a touchscreen.

17. The method of claim 9, further comprising accessing one or more test sound segments stored in memory of the hearing device.

18. The method of claim 17, further comprising receiving a wireless command from the computing device, wherein the one or more test sound segments accessed are selected based on the wireless command.

19. A method of self-fitting of a hearing device, the method comprising: providing a hearing device comprising memory storing test sound segments representative of a loud sound and a soft sound, wherein the test sound segments correspond to suprathreshold loudness level s within an audible range of human hearing; receiving a wireless command to produce a test output representative of one or more test sound segments; producing, by the hearing device in-situ, the test output representative of the one or more test sound segments stored within memory of the hearing device in response to receiving the wireless command, wherein the test output is at least partially based on fitting parameters programmed into the hearing device, receiving, by a computing device communicatively coupled to the hearing device, user input indicative of a consumer's assessment of the test output: and adjusting a plurality of the fitting parameters based, at least in part, on the consumer's assessment of the test output, wherein the adjusting comprises making a first adjustment to one or more fitting parameters corresponding to the loud level sound and making a second adjustment to one or more fitting parameters corresponding to the soft level sounds wherein at least one of the first adjustment or the second adjustment is performed while the test output is being produced.

20. The method of claim 19, wherein the consumer's assessment is registered by a keyboard, a mouse, or a touchscreen.

21. The method of claim 19, further comprising transmitting, by the computing device, the wireless command to the hearing device.

\* \* \* \* \*